United States Patent
Digby et al.

(10) Patent No.: US 6,440,664 B1
(45) Date of Patent: Aug. 27, 2002

(54) APPARATUS FOR SEQUENCING OF NUCLEIC ACIDS USING MULTIPLE DYES

(75) Inventors: Thomas J. Digby; Alexandre Izmailov, both of Toronto (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 09/213,384

(22) Filed: Dec. 9, 1998

Related U.S. Application Data

(62) Division of application No. 08/634,284, filed on Apr. 18, 1996.

(51) Int. Cl.[7] ............... C12Q 1/68; C12M 1/36; G01N 15/06; G01N 21/64; C02F 1/40

(52) U.S. Cl. ............ 435/6; 435/283.1; 435/286.1; 435/287.1; 435/287.2; 422/50; 422/61; 422/68.1; 422/82.05; 422/82.08; 544/244; 544/243; 204/612; 356/344

(58) Field of Search ............ 435/6, 283.1, 286.1, 435/287.1, 287.2; 544/244, 243; 204/612; 356/344; 422/50, 61, 68.1, 82.05, 82.08

(56) References Cited

U.S. PATENT DOCUMENTS

| | | | |
|---|---|---|---|
| 4,811,218 A | 3/1989 | Hunkapiller et al. | ... 364/413.01 |
| 4,832,815 A | 5/1989 | Kambara et al. | ........ 204/299 R |
| 5,062,942 A | 11/1991 | Kambara et al. | ........ 204/299 R |
| 5,124,247 A * | 6/1992 | Ansorge | ..................... 435/6 |
| 5,171,534 A | 12/1992 | Smith et al. | ............. 422/82.05 |
| 5,190,632 A | 3/1993 | Fujimiya et al. | ........ 204/299 R |
| 5,207,880 A | 5/1993 | Middendorf et al. | ..... 204/182.8 |
| 5,213,673 A | 5/1993 | Fujimiya et al. | ........ 204/299 R |

(List continued on next page.)

OTHER PUBLICATIONS

Olesen, et al. "Chemiluminescent DNA Sequencing with Multiplex Labeling" Biotechniques 15: 480–485, 1993.*

Wiemann et al. "Simultaneous on–line DNA sequencing on both strands with two fluorescent dyes" 1995, Analytical Biochemistry. 224:117–121.*

Stratagene catalog, 1988, p. 39.*

Sanger et al., "DNA Sequencing with chain–terminating inhibitor", *Proc. Natl Acad Sci USA* 74: 5463–5467 (1977).

Maxam et al., "A new method for sequencing DNA", *Proc. Natl Acad Sci USA* 74: 560–564 (1977).

Smith et al., "Fluorescence detection in automated DNA sequence analysis", *Nature* 321: 674–679 (1986).

Wiemann et al., "Simultaneous On–Line DNA Sequencing on Both Strands with Two Fluorescent Dyes", *Anal. Biochem.* 224: 117–121 (1995).

Kambara et al., "Real Time Automated Simultaneous Double–Stranded DNA Sequencing Using Two–Color Fluorophore Labeling", *Bi/Technology* 9: 648–651 (1991).

Olesen et al., "Chemiluminsecent DNA sequencing with multiplex labeling", *Biotechniques* 15: 480–485 (1993).

Wiemann et al., "Doublex fluorescent DNA sequencing: two independent sequences obtained simultaneously with one reaction with internal labeling an unlabeled primers", *Anal. Biochem* 234: 166–174 (1996).

(List continued on next page.)

*Primary Examiner*—W. Gary Jones
*Assistant Examiner*—B J Forman
(74) *Attorney, Agent, or Firm*—Oppedahl & Larson LLP

(57) ABSTRACT

An instrument for sequencing oligonucleotides is loaded with the products of four sequencing reaction mixtures. These products are a combination of A, C, G and T reaction products for several sequencing reactions. The products of the different sequencing reactions are labeled with fluorescent tags which are distinguishable one from the other on the basis of their excitation or emission spectra. After separation of the oligonucleotides by electrophoresis, the order of the detected peaks is used to call the base sequence.

1 Claim, 5 Drawing Sheets

U.S. PATENT DOCUMENTS

| | | | |
|---|---|---|---|
| 5,290,419 A | | 3/1994 | Kambara et al. ........ 204/299 R |
| 5,307,148 A | | 4/1994 | Kambara et al. ............ 356/344 |
| 5,360,523 A | | 11/1994 | Middendorf et al. ...... 204/182.8 |
| 5,427,911 A | * | 6/1995 | Ruano ............................ 435/6 |
| 5,608,063 A | * | 3/1997 | Hobbs et al. ................ 544/244 |

OTHER PUBLICATIONS

Creasey et al., "Application of a novel chemiluminescence–based DNA detection method to a single–vector and multi-plex DNA sequencing" *Biotechniques* 11: 102–109 (1991).

* cited by examiner

APPARATUS FOR SEQUENCING OF NUCLEIC ACIDS USING MULTIPLE DYES

This application is a divisional of copending U.S. patent application Ser. No. 08/634,284 filed Apr. 18, 1996.

BACKGROUND OF THE INVENTION

This application relates to an improved method for sequencing of nucleic acids using multiple fluorescent labels, and to apparatus and kits adapted for use with the method.

Sequencing of nucleic acids using the chain termination method involves the general steps of combining the target nucleic acid polymer to be sequenced with a sequencing primer which hybridizes with the target nucleic acid polymer; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. Analysis of fragments may be done by electrophoresis, for example on a polyacrylamide gel.

Although this type of analysis was originally performed using radiolabeled fragments which were detected by autoradiography after separation, modern automated DNA sequencers generally are designed for use with sequencing fragments having a fluorescent label. The fluorescently labeled fragments are detected in real time as they migrate past a detector.

U.S. Pat. No. 5,171,534 which is incorporated herein by reference describes a variation of this basic sequencing procedure in which four different fluorescent labels are employed, one for each sequencing reaction. The fragments developed in the A, G, C and T sequencing reactions are then recombined and introduced together onto a separation matrix. A system of optical filters is used to individually detect the fluorophores as they pass the detector. This allows the throughput of a sequencing apparatus to be increased by a factor of four, since the four sequencing reaction which were previously run in four separate lanes or capillaries can now be run in one.

It is an object of the present invention to provide a further improvement for use with chain termination sequencing reactions which can further increase the throughput of an instrument.

SUMMARY OF THE INVENTION

In order to use nucleic acid sequencing as a diagnostic tool, it will be necessary to determine the sequence of the same DNA region from many samples. The present invention makes it possible to increase the throughput of an instrument being used for this purpose. Thus, a first aspect of the invention provides a method for evaluating the sequence of a target nucleic acid polymer in a plurality of samples. In this method, each sample is first divided into four aliquots which are combined with four sequencing reaction mixtures. Each sequencing reaction mixture contains a polymerase enzyme, a primer for hybridizing with the target nucleic acid, nucleotide triphoshate feedstocks and a different dideoxynucleotide triphosphate. This results in the formation of an A-mixture, a G-mixture, a T-mixture and a C-mixture for each sample containing product oligonucleotide fragments of varying lengths. The product oligonucleotide fragments are labeled with fluorescent tags, and these tags will generally be the same for all four sequencing reactions for a sample. However, the fluorescent tags used for each sample are distinguishable one from the other on the basis of their excitation or emission spectra.

Next, the A-mixtures for each sample are combined to form a combined A mixture, the G-mixtures are combined to form a combined G-mixture and so on for all four mixtures. The combined mixtures are loaded onto a separation matrix at separate loading sites and an electric field is applied to cause the product oligonucleotide fragments to migrate within the separation matrix. The separated product oligonucleotide fragments having the different fluorescent tags are detected as they migrate within the separation matrix.

The method of the invention can be used as described above to determine the position of every base in the sequence, or it can be used to determine the position of less than all four bases. For example, the method can be used to determine the position of only the A bases within a sequence for some diagnostic applications.

A further aspect of the present invention is a kit useful for diagnostic sequencing of a selected portion of a gene. One embodiment of such a kit contains a plurality of sequencing primers for the selected portion of the gene, each sequencing primer being identical in its DNA sequence but being labeled with a different fluorescent tag.

A further aspect of the invention is an apparatus for performing the method of the invention. Such an apparatus comprises (a) means for providing excitation energy to a detection site within a separation matrix disposed within the apparatus;

(b) means for detecting light emitted from fluorescently-labeled oligonucleotide fragments located within the detection site;

(c) configuration control means, operatively connected to the means for providing excitation energy and the means for detecting to provide combinations of excitation wavelength and detection wavelength specific for a plurality of different fluorescently-labeled oligonucleotide fragments; and (d) data processing means, operatively connected to the configuration control means and the means for detecting for receiving a signal from the means for detecting and assigning that signal to a data stream based upon the combination of excitation wavelength and detection wavelength set by the configuration control means.

DETAILED DESCRIPTION OF THE INVENTION

Figure 1A:
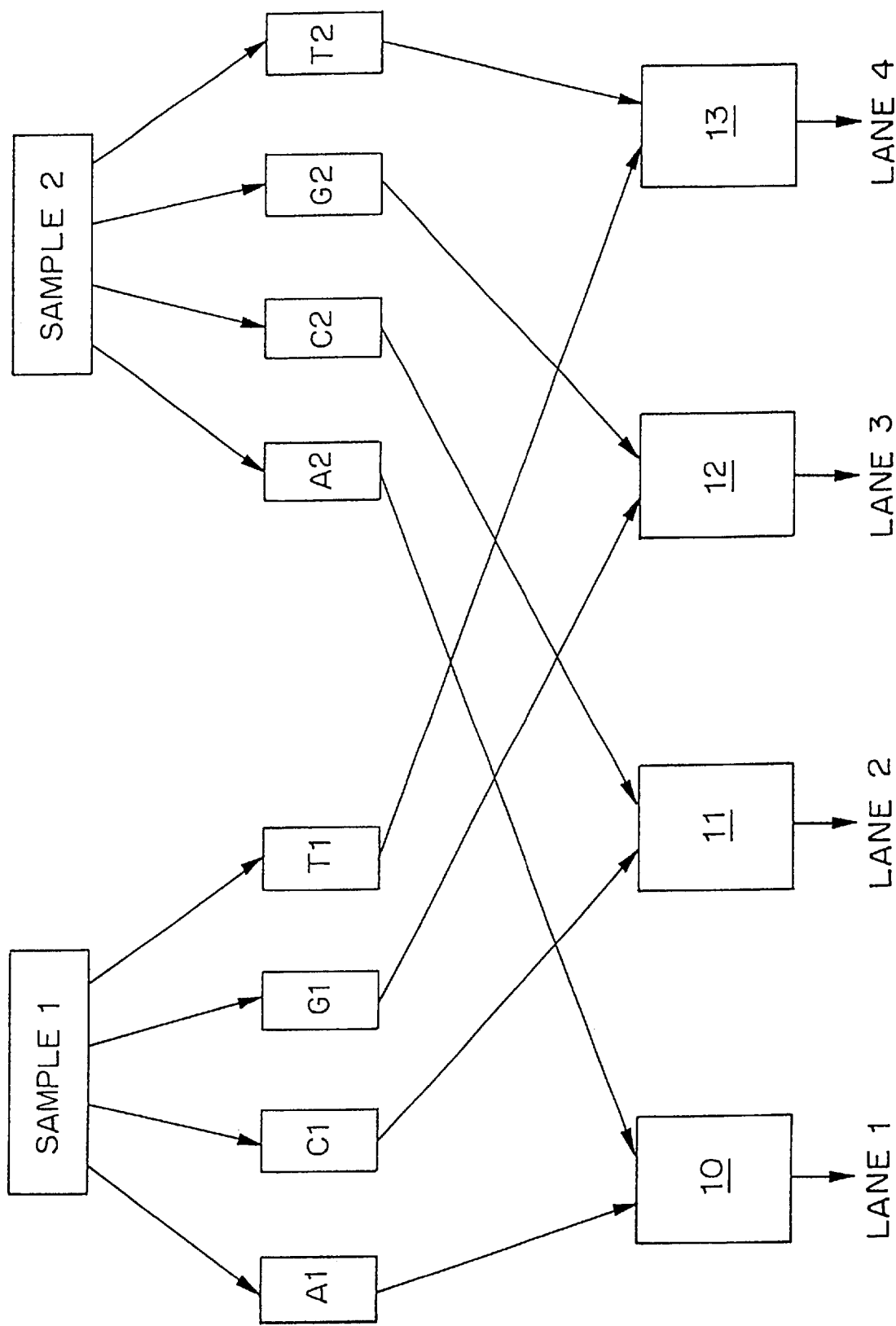
FIGS. 1 A and B shows a schematic representation of the method of the invention.

FIG. 1A shows a schematic representation of one embodiment of the method of the invention. The figure depicts the application of the method to two samples for clarity. As will be apparent from the discussion below, however, the method of the invention is not limited to two samples, and is in fact preferably applied for four or more samples, up to a limit imposed only by the number of distinguishable tags which can be identified.

As shown in FIG. 1A, two samples, "sample 1" and "sample 2" are each divided into four aliquots and these aliquots are introduced into sequencing reactions A1, C1, C1, and T1, and A2, C2, G2 and T2. Each sequencing reaction contains the reagents necessary for producing product oligonucleotide fragments of varying lengths indicative of the position of one-base within the target nucleic acid sequence. These reagents include a polymerase enzyme, for example T7 polymerase, Sequenase™, Thermo Sequenase™, or the Klenow fragment of DNA polymerase; A, C, G and T nucleoside feedstocks; one type of chain terminating dideoxynucleoside; and a sequencing primer.

After the product oligonucleotide fragments are formed in each reaction mixture, the products from reaction mixture A1 are combined with the products from reaction mixture A2 to form a combined mixture 10 which is loaded onto lane 1 of a separation matrix. Likewise, the products from reaction mixture C1 are combined with the products from reaction mixture C2 to form a combined mixture 11 which is loaded onto lane 2 of the separation matrix; the products from reaction mixture G1 are combined with the products from reaction mixture G2 to form a combined mixture 12 which is loaded onto lane 3 of the separation matrix; and the products from reaction mixture T1 are combined with the products from reaction mixture T2 to form a combined mixture 13 which is loaded onto lane 4 of the separation matrix.

The key to the present invention is the use of labels in the reactions A1, C1, G1, and T1 which are distinguishable from the labels used in reactions A2, C2, G2 and T2, respectively. Thus, unlike the method described in U.S. Pat. No. 5,171,534 where the labels used for the A, C, G, and T reactions for a sample are distinct, in the present invention the labels used for the four sequencing reactions for any one sample can be, and preferably are, the same. Instead, it is the labels which are used in the several samples which are distinct in the method of the invention.

Figure 1B:
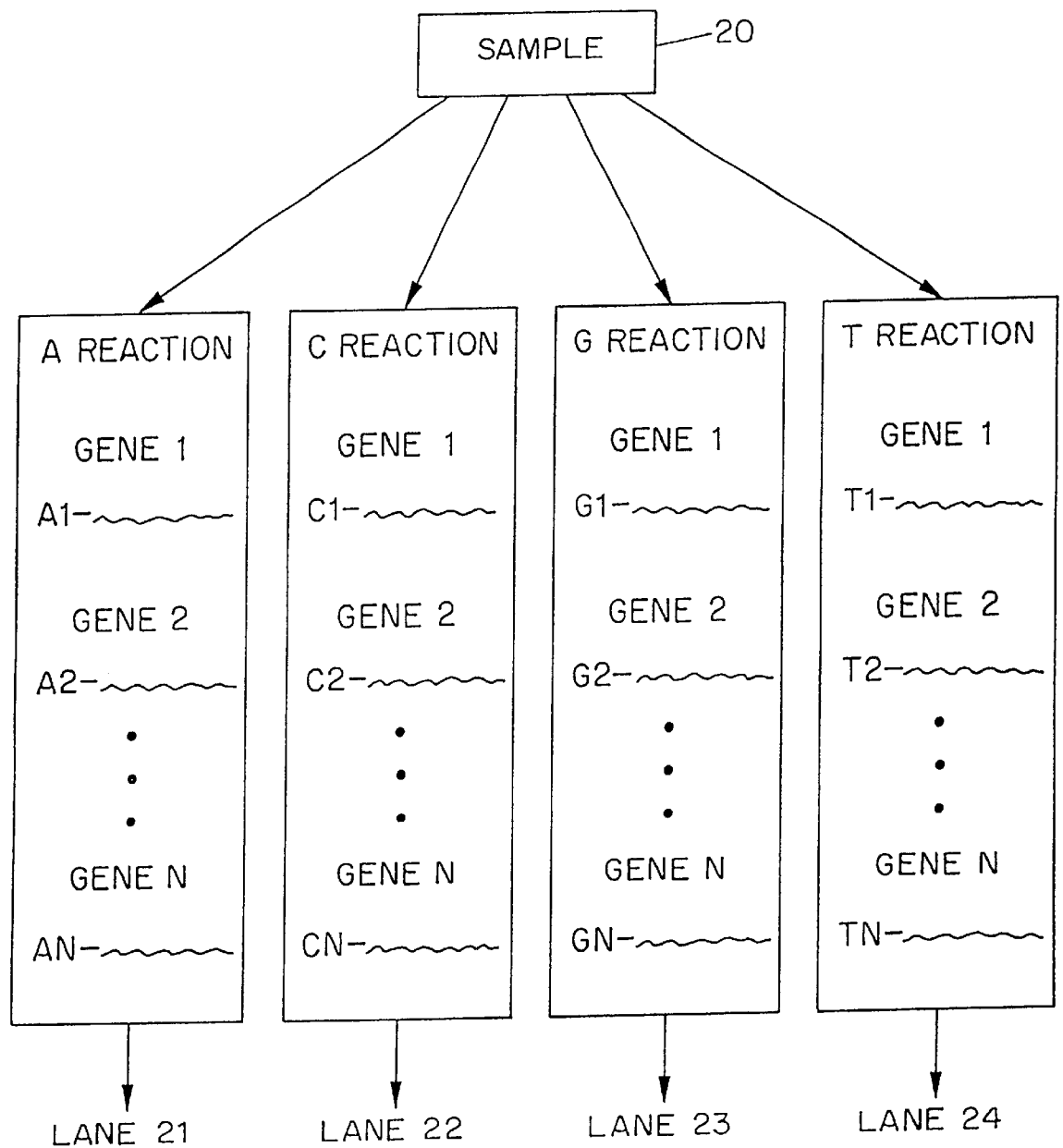

An alternative embodiment of the invention is illustrated in FIG. 1B. In this case, the operator wants to sequence a plurality of genes (or different exons of the same gene) from one patient sample. The sample 20 is divided into four aliquots. A sequencing reaction mix containing the reagents necessary for producing product oligonucleotide fragments of varying lengths is added to each aliquot. The sequencing mix added to a first aliquot contains all of the reagents for an A termination reaction, plus a plurality of. sequencing primers, each one labeled with a distinguishable fluorophore, and each one being specific for a different gene (or different exon of the same gene). The sequencing mix added to a second aliquot contains all of the reagents for a C termination reaction, plus the same plurality of sequencing primers. Sequencing reaction mixes for G and T are made in the same fashion. These sequencing mixture are reacted to produce oligonucleotides fragments, and then loaded onto lanes 21, 22, 23, and 24 of a sequencing gel and separated. Using this technique, any number of genes or exons in a sample can be simultaneously sequenced up to the limit imposed by the number distinguishable tags which can be identified.

Suitable labels for use in the present invention are fluorescent tags. These can be incorporated into the product oligonucleotide fragments in any way, including the use of fluorescently tagged primers or fluorescently tagged chain terminating reagents.

Figure 2A:
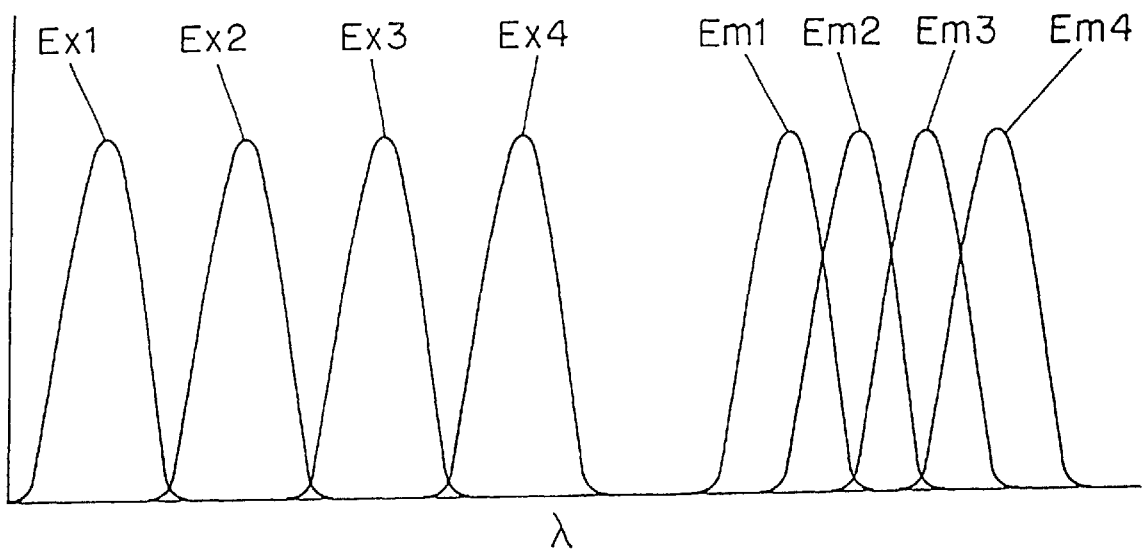
FIGS. 2 A, B, C, and D show excitation and emission spectra for theoretical sets of useful fluorescent tags.
Figure 2B:
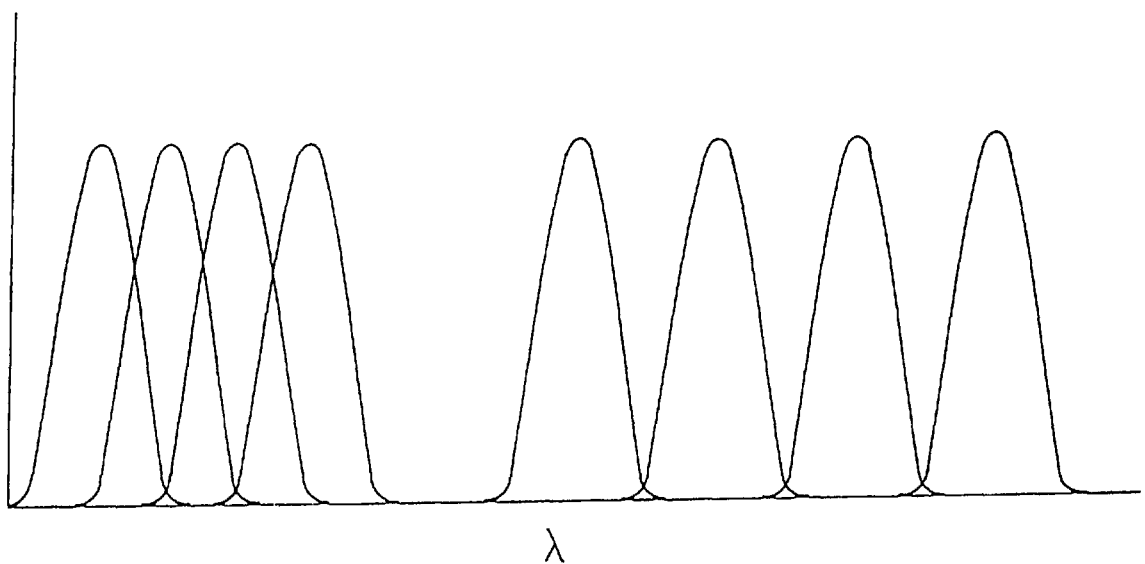
Figure 2C:
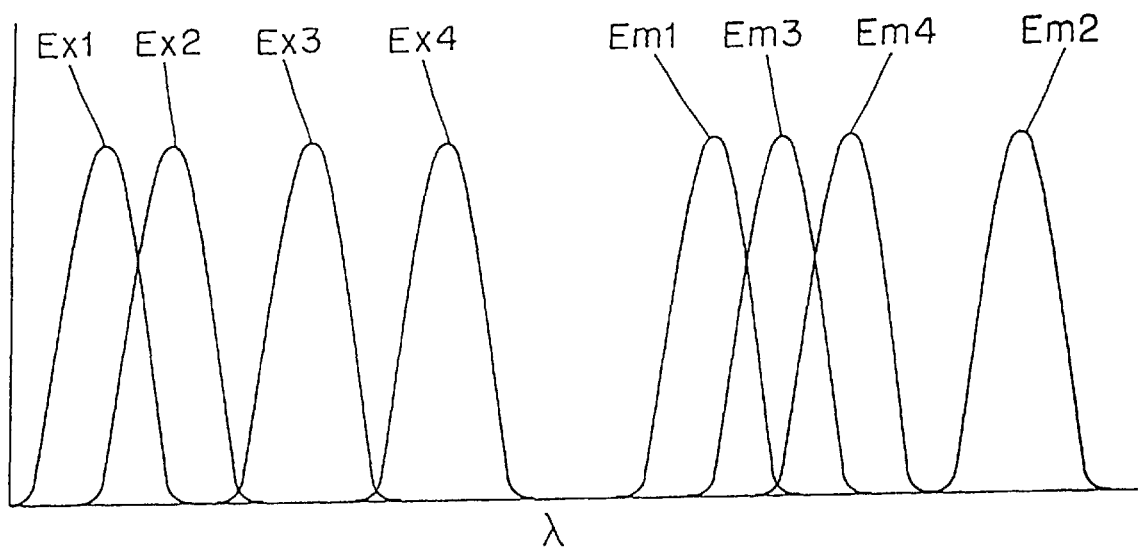
Figure 2D:
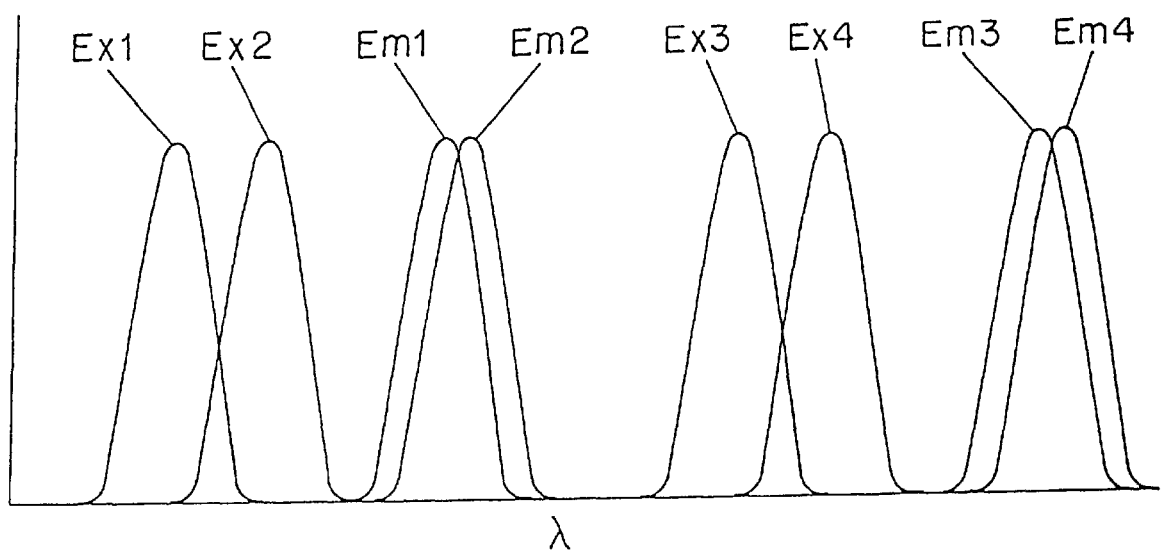

The fluorescent tags selected for use in the present invention must be distinguishable one from another based on their excitation and/or emission spectra. For example, as shown in FIG. 2A, a set of tags could be selected which had overlapping emission spectra (Em1, Em2, Em3 and Em4) but separate and distinguishable excitation spectra (Ex1, Ex2, Ex3, and Ex4). A set of tags could also be selected which had overlapping excitation spectra but separate and distinguishable emission spectra as shown in FIG. 2B. Further, as shown in FIG. 2C, a set of tags could be selected in which some of the tags have overlapping excitation spectra (Ex1 and Ex2) but separate and distinguishable emission spectra (Em1 is distinguishable from Em2); while the others have separate and distinguishable excitation spectra (Ex1, Ex3, and Ex4) but overlapping emission spectra (Em1, Em3 and Em4). A further combination of excitation and emission spectra is shown in FIG. 2D.

Examples of sets of suitable tags, together with the wavelength maximum for the excitation and emission spectra are shown in Table 1. Many other fluorophores are available that can be used as labels for DNA sequencing reaction products. Such dyes are available from Applied Biosystems, Inc. (Foster City, Calif.), Molecular Probes, Inc. (Oregon) and others.

TABLE 1

Fluorescent Dye's suitable for use with the invention

| Fluorescent Dye | Excitation Max (nm) | Emission Max (nm) |
|---|---|---|
| Texas Red X | 599 | 617 |
| Carboxy-X-Rhodamine | 585 | 612 |
| CarboxyFluorescein | 494 | 521 |
| CarboxyTetraMethylRhodamine | 561 | 591 |
| Carboxycyanine 5.0 | 650 | 667 |

Figure 3:
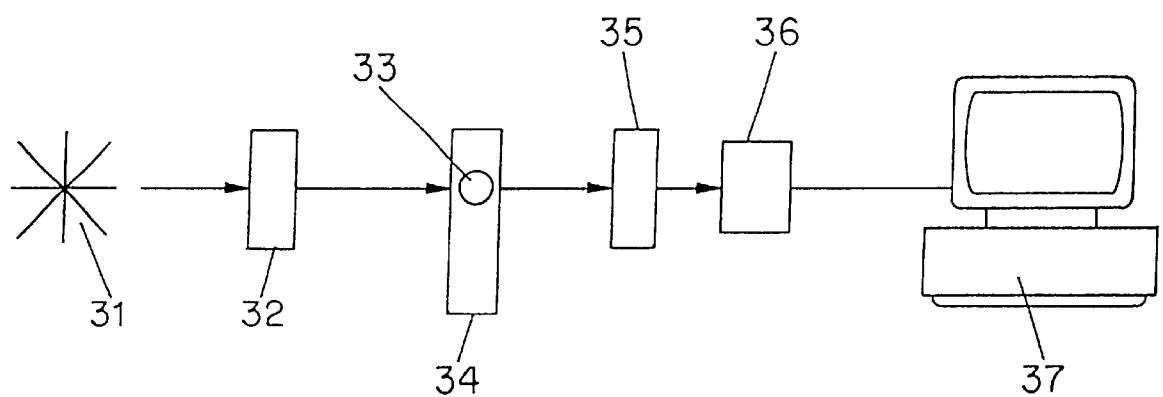
FIG. 3 shows an apparatus for evaluating the sequence of nucleic acid polymers using the method of the invention.

FIG. 3 shows a basic layout for an apparatus for evaluating the sequence of nucleic acid polymers using the method of the invention. Light from a light source 31, which may be for example a laser, a light emitting diode, a laser diode, an incandescent or polychromatic lamp, or any combination of such sources, is passed through an optical filter 32 to select an appropriate excitation wavelength which is directed to a detection site 33 in a separation matrix 34. Light emitted by fluorescent tags in the detection site 33 passes through a second optical filter 35 to a detector 36. Either or both of the optical filters 32 and 36 may be adjustable under the control of a microprocessor, minicomputer or personal computer 37 to provide various configurations of excitation and emission wavelengths as discussed more fully below. The output from the detector is then transmitted to a data processing system such as a dedicated microprocessor, minicomputer or personal computer 37 for analysis to produce a report on the sequence of the sample being evaluated.

In the case where the properties of the selected tags are of the type shown in FIG. 2A, the optical filter 32 may adjustable, for example by rotating several different filters through the path of the excitation beam, to produce excitation beams corresponding to the different excitation wavelengths of the tags. Optical filter 35 may then be simply a cut-off filter selected to exclude light of the excitation wavelengths from the detector. Information concerning the position of the optical filter 32 as a function of time is transmitted to the data processing system, and used to permit interpretation of the fluorescence data. Thus, when the optical filter 32 is in a position that corresponds to the excitation spectrum of the tag used to label sample 1, the data processing system interprets the emission intensity as data for the sequence of sample 1; when the optical filter 32 is in a position that corresponds to the excitation spectrum of the tag used to label sample 2, the data processing system interprets the emission intensity as data for the sequence of sample 2 and so on for as many different tags are used.

In the case where the properties of the selected tags are of the type shown in FIG. 2B, the optical filter 35 is adjustable, for example by rotating several different filters through the path of the excitation beam, to selectively collect emission wavelengths corresponding to the different tags. Optical filter 32 may be simply a cut-off or band-pass filter selected to exclude light of the emission wavelengths from the detector. Information concerning the position of the optical filter 35 as a function of time is transmitted to the data processing system, and used to permit interpretation of the fluorescence data. Thus, when the optical filter 35 is in a position that corresponds to the emission spectrum of the tag used to label sample 1, the data processing system interprets the emission intensity as data for the sequence of sample 1; when the optical filter 35 is in a position that corresponds to the emission spectrum of the tag used to label sample 2, the data processing system interprets the emission intensity as data for the sequence of sample 2 and so on for as many different tags are used.

Finally, in the case where the properties of the selected tags are of the type shown in FIG. 2C, both optical filter 32 and optical 35 are adjustable in synchronization to control the excitation and emission wavelengths being monitored. Information concerning the position of the optical filters 32 and 35 as a function of time is transmitted to the data processing system, and used to permit interpretation of the fluorescence data. Thus, when optical filter 32 is in a position that corresponds to excitation spectrum Ex1 in FIG. 2C, and optical filter 35 is in a position that transmits the light of the wavelength of emission spectrum Em1, the data processing system interprets the emission intensity as data for the sequence of the sample labeled with tag 1. When the optical filter 35 is in a position to transmit light of the wavelength of emission spectrum Em2, on the other hand, the data processing system interprets the emission intensity as data for the sequence of the of sample labeled with tag 2.

The light source 31 may be a single light source which is moved across the gel to irradiate each detection zone individually, for example as described in U.S. Pat. No. 5,207,880 which is incorporated herein by reference. The light source 31 may also be a singe light source which is split into multiple beamlets, for example using optical fibers or through the use of a beam splitter such as a spot array generation grating to each of the detection sites as described generally in U.S. patent application Ser. No. 08/353,932 and PCT Patent Application No. PCT/US95/15951 which are incorporated herein by reference. The light source 31 may also be multiple individual light sources, each of which irradiates a subset of one or more of the detection sites within the separation matrix.

While optical filter 32 described above can be used effectively to provide selection of excitation wavelength, it will be understood that other approaches to providing different excitation wavelengths can be used as well. For example a plurality of lasers of different wavelengths could be used, with the light from each directed in turn to the detection site. For detection of product oligonucleotide fragments in multiple lanes of an electrophoresis gel, one set of lasers might be used (one for each necessary wavelength) with light from each of the lasers being conducted by optical fibers or through the use of a beam splitter such as a spot array generation grating to each of the detection sites as described generally in U.S. patent application Ser. No. 08/353,932 and PCT Patent Application No. PCT/US95/15951. Optical switches, operatively connected to the data processing system, are used to select which of the excitation wavelengths is striking the detection zone at any given time, in the same manner as a rotating optical filter could do. A detector assembly which scans across the lanes of an electrophoresis gel could also be used, for example as described in U.S. Pat. Nos. 5,360,523 and 5,100,529, which are incorporated herein by reference, although the time required for such a device to scan all the lanes of a gel may be a limiting factor in applications with short total migration times.

It will also be appreciated that multiple optical filters mounted on individual detectors could be used in place of the adjustable optical filter 35 and the single detector 36 shown in FIG. 3. Similarly several detectors with adjustable optical filters might also be used.

Other optical components which separate light by wavelength may also be used in place of optical filter 35. Thus, for example, a diffraction grating or prism which spatially separates light of differing wavelength may be employed. In this case, radiation from the different fluorophores will be distributed in space, and can be detected by dedicated detectors such as photodiodes, CCD elements (linear or X-Y). Similarly, distinct optical filters for each wavelength can be employed in combination with a multiplicity of detectors. Optical filters which are transmissive at the emission wavelength of one fluorophore and reflective at the emission wavelength of a second fluorophore can also be used to direct emitted light to separate detectors depending on wavelength.

The detectors used in the apparatus of the invention may be photomultipliers, photodiodes or a CCD. As noted above, the apparatus can be configured with one or more detectors for each detection site. The apparatus can also be configured such that one detector overlaps with several detection sites if the excitation light is directed to the detection sites one at a time. In addition, the apparatus can use a single detector (or a small array of detectors) which is scanned across the gel during detection.

For determining the sequence of a selected region of DNA using the method of the invention, a kit may be formulated. Such a kit comprises, in packaged combination, a plurality of containers, each containing a reagent for the sequencing of the selected region of DNA. The reagent in each container has a reactive portion, which is involved in the sequencing reaction, and a fluorescent label portion. The label portions of the reagents in each container are different and distinguishable one from the other on the basis of the excitation or emission spectra thereof.

In a preferred embodiment, a kit in accordance with the invention comprises a plurality of primers for sequencing the selected region, each of the primers having a different and distinguishable fluorescent label. Thus, the reactive portions of the reagents in this case are the oligonucleotide primer to which the labels are attached. The reactive portions may be different from one another, but are preferably the same. Such a kit may also include additional reagents for sequencing, including polymerase enzymes, dideoxynucleotide triphosphates and buffers.

Alternatively, the kit may contain one primer for the selected region and a plurality of containers of chain-terminating nucleotide triphosphates, each labeled with a different and distinguishable fluorescent label. In this case, the reactive portion of the reagent is the chain terminating nucleotide triphosphate which can be incorporated in place of a normal nucleotide triphosphate during the sequencing reaction. The kit may include reagents having just one type of chain-terminating nucleotide triphosphate, for example ddA with a plurality of distinct fluorescent labels, or it may include reagents having two or more types of chain-terminating nucleotide triphosphate, each with a plurality of distinct labels. Such a kit may also include additional reagents for sequencing, including polymerase enzymes and buffers, as well as additional chain-terminating nucleotide triphosphate (single-labeled) for those not provided as part of a multi-label reagent set.

For practising the method shown in FIG. 1B, a suitable kit in accordance with the invention includes at least one container containing a mixture of a plurality of sequencing primers, one for each gene region to be evaluated. The plurality of sequencing primers each comprise a reactive portion which hybridizes with DNA in the sample and a label portion, the label portions of the reagents being different and distinguishable one from the other. Preferably, the detectable labels are fluorescent tags, distinguishable one from the other by their emission or excitation spectra.

What is claimed is:

1. An apparatus for evaluating the sequence of a nucleic acid polymer by separation of a reaction mixture containing fluorescently-labeled oligonucleotide fragments in a separation matrix disposed within the apparatus, said oligonucleotide fragments reflecting by their lengths positions of bases within the nucleic acid polymer, said apparatus comprising (a) means for providing excitation energy to a detection zone within the separation matrix to induce emission of light from the fluorescently-labeled oligonucleotide fragments;

(b) means for detecting light emitted from fluorescently-labeled oligonucleotide fragments located within the detection zone to produce a data signal, said data signal comprising a plurality of peaks including at least some peaks representing emission from fluorescently-labeled oligonucleotide fragments with two or more different label types;

(c) configuration control means for controlling and synchronizing the means for providing excitation energy, and the means for detecting, said configuration control means providing a plurality of combinations of excitation wavelength and detection wavelength, one specific for each of a plurality of different fluorescent label types; and (d) data processing means for receiving the data signal from the means for detecting and a configuration signal from the configuration control means providing an indication of the combination of excitation and emission associated with each peak in the data signal, and for assigning each peak to a data set associated with one of the plurality of different fluorescent label types based upon the combination of excitation wavelength and detection wavelength set by the configuration control means.

* * * * *